(12) United States Patent
Zinger

(10) Patent No.: US 6,234,994 B1
(45) Date of Patent: May 22, 2001

(54) MULTICOMPONENT TISSUE ADHESIVE APPLICATION DEVICE AND HOLDER FOR SUCH DEVICE

(75) Inventor: Freddy Zinger, Raanana (IL)

(73) Assignee: Omrix Biopharmaceuticals SA, Brussels (BE)

( * ) Notice: Subject to any disclaimer, the term of this patent is extended or adjusted under 35 U.S.C. 154(b) by 0 days.

(21) Appl. No.: 09/254,554

(22) PCT Filed: Sep. 9, 1997

(86) PCT No.: PCT/EP97/04919

§ 371 Date: May 10, 1999

§ 102(e) Date: May 10, 1999

(87) PCT Pub. No.: WO98/10704

PCT Pub. Date: Mar. 19, 1998

(30) Foreign Application Priority Data

Sep. 10, 1996 (DE) .............................................. 196 36 622

(51) Int. Cl.[7] .................................................. A61M 37/00
(52) U.S. Cl. .............................. 604/82; 604/191; 222/137
(58) Field of Search ................ 604/82–86, 181–182, 604/183, 187, 191; 222/145.5, 145.6, 137, 386

(56) References Cited

U.S. PATENT DOCUMENTS

| | | | |
|---|---|---|---|
| 3,767,085 | * 10/1973 | Cannon et al. . | |
| 4,359,049 | 11/1982 | Redl et al. . | |
| 4,631,055 | * 12/1986 | Redl et al. . | |
| 4,753,536 | * 6/1988 | Spehar et al. . | |
| 4,874,368 | 10/1989 | Miller et al. . | |
| 4,978,336 | 12/1990 | Capozzi et al. . | |
| 5,104,375 | * 4/1992 | Wolf et al. . | |
| 5,290,259 | * 3/1994 | Fischer . | |
| 5,445,614 | * 8/1995 | Haber et al. . | |
| 5,582,596 | * 12/1996 | Fukunaga et al. . | |
| 5,643,206 | * 7/1997 | Fischer . | |

FOREIGN PATENT DOCUMENTS

| | | |
|---|---|---|
| 4223356 | 1/1994 | (DE) . |
| 29509729 | 8/1995 | (DE) . |
| 0037393 | 1/1983 | (EP) . |
| 0689874 | 1/1996 | (EP) . |
| 9218176 | * 10/1992 | (WO) . |
| 9531137 | * 11/1995 | (WO) . |

\* cited by examiner

*Primary Examiner*—Anh-Tran T. Nguyen
*Assistant Examiner*—LoAn H. Thanh
(74) *Attorney, Agent, or Firm*—Birch, Stewart, Kolasch & Birch, LLP

(57) ABSTRACT

An application device for applying a multicomponent tissue adhesive which includes a plurality of supply reservoirs for respectively one fluid component, each supply reservoir having a front end with an opening for discharge of the respective fluid component. The front ends of the supply reservoirs are arranged within accommodating connecting pieces of a connecting headpiece. The accommodating connecting pieces are provided with projections extending radially outwards. The supply reservoirs are held by a holding device. The application device is further provided with a coupling element for releasably connecting the holding device to the connecting headpiece, the coupling element including an encompassing member with a plurality of encompassing zones for at least partially encompassing the accommodating connecting pieces and for abutment on the sides of the projections of the accommodating connecting pieces facing away from the holding device.

30 Claims, 2 Drawing Sheets

MULTICOMPONENT TISSUE ADHESIVE APPLICATION DEVICE AND HOLDER FOR SUCH DEVICE

This application is the national phase under 35 U.S.C. §371 of prior PCT International Application No. PCT/EP97/04919 which has an International filing date of Sep. 9, 1997 which designated the United States of America.

BACKGROUND OF THE INVENTION

The present invention relates to an application device for applying a multicomponent tissue adhesive. The invention further relates to a holding device for keeping the supply reservoirs and a connecting headpiece, having the supply reservoirs coupled thereto, attached to each other.

An application device for applying a multicomponent tissue adhesive is known from U.S. Pat. No. 4,874,368, U.S. Pat. No. 4,978,336, U.S. Pat. No. 5,104,375 and EP-B-0 037 393, respectively. In these known application devices, the two supply reservoirs containing the adhesive components are held together by a holding device which makes it possible to hold the application device between the fingers of a hand and to operate the device by one hand. The conically tapering outlet connecting pieces of the two supply reservoirs are inserted into the accommodating connecting pieces of a connecting headpiece, wherein the accommodating connecting pieces are arranged as syringes with cylinders and pistons. Since these outlet connecting pieces have an inner cone of the same angle as the outer cone of the supply-reservoir outlet connecting pieces, the connecting pieces of the supply reservoir become wedged with those of the connecting headpiece, thus resulting in a certain axial securing effect of this coupling connection. However, this axial retentive force may be too small if the channels extending through the connecting headpiece from the accommodating connecting pieces up to a common discharge end are clogged. Thus, when actuating the pistons, the connecting headpiece may become detached from the supply reservoirs because of the pressure build-up within the supply reservoirs, rendering the application device inoperable.

For this reason, it is provided in another known application device described in WO-A-95/31137 that the connecting head is mechanically secured by a coupling element on the holding device to thus preclude undesired detachment from the outlet connecting pieces of the supply reservoirs. The coupling element of this known application device is lockingly inserted into openings of the connecting headpiece and the holding device. Although this connection is mechanically reliable, it can be released only with difficulties, which can be desirable e.g. to allow a quick refill of the supply reservoirs. In the commercially available tissue adhesive application system Duploject (Duploject is a registered trademark) of the Immuno company the connecting headpiece has a connecting strip elastically attached thereto, wherein the free end of the connecting strip facing away from the connecting headpiece is provided with a bore. The free end is adapted for mounting on a pin of the holding device. The mechanical connecting of the connecting strip to the holding device requires a certain precision in handling, which may be disturbing.

SUMMARY OF THE INVENTION

It is the object of the invention to provide an application device and a holding device for this application device wherein the connecting headpiece can be releasably connected to the holding device of the supply reservoirs for thus securing it against unintended detachment from the supply reservoirs, and wherein this mechanical connection, although providing a safe hold, can be released and established easily and without problems.

For solving the above object, the invention provides an application device comprising a plurality of supply reservoirs for respectively one fluid component, particularly a tissue adhesive component, each supply reservoir having a front end with an opening for discharge of the respective fluid component and a rear end opposite to the front end, and a piston arranged for sliding displacement in the supply reservoir, with the piston comprising a piston rod projecting from the rear end and having an actuating end for actuating the piston, a connecting headpiece having accommodating connecting pieces for the front ends of the supply reservoirs, the connecting headpiece having channels for the individual fluid components extending therethrough between the inlet openings thereof and a discharge end for simultaneous discharge of all fluid components, and the accommodating connecting pieces being provided with radially outward projections, a holding device for holding the supply reservoirs in the region of their rear ends, the holding device being adapted to be positioned between the fingers of a hand, and a coupling element for releasably connecting the holding device to the connecting headpiece, the coupling element comprising an encompassing member with a plurality of encompassing zones for at least partially encompassing the accommodating connecting pieces and for abutment on the sides of the projections of the accommodating connecting pieces facing away from the holding device.

The holding device according to the invention is provided with a holding device for holding supply reservoirs for the individual fluid components, the holding device being adapted to be positioned between the fingers of a hand, and a coupling element for releasably connecting the holding device to a connecting headpiece which is adapted to have the supply reservoirs coupled thereto and which is provided for simultaneous discharge of all fluid components, the coupling element comprising an encompassing member with a plurality of encompassing zones for partially encompassing connecting pieces of the connecting headpiece provided with outer projections, and for gripping engagement behind the outer projections of the connecting pieces of the connecting headpiece.

According to the invention, the application device comprises a coupling element, connected with the holding device, which is provided with an encompassing member arranged to encompass accommodating connecting pieces of the connecting headpiece at least partially and particularly through a peripheral angular range between about 200° and 300°. In doing so, the encompassing member is in engagement behind projections arranged on the accommodating connecting pieces of the connecting headpiece; thus, the encompassing member is in abutment on that side of these projections which is facing away from the holding device. In this manner, the encompassing member prevents a detachment of the connecting headpiece from the outlet connecting pieces of the supply reservoir.

The positioning of the encompassing member can be performed in a particularly simple manner if the encompassing zones surrounding the accommodating connecting pieces are elastic so that the encompassing member can be mounted to the accommodating connecting pieces from the side. Because of the elastic resiliency of the encompassing zones, arranged particularly as C-shaped brackets extending around the accommodating connecting pieces through 200° to 300°, the encompassing member in its mounted condition is kept from undesirably sliding laterally off the accommodating connecting pieces.

Preferably, the encompassing member is connected to the holding device by a connecting member which is particularly provided as a preferably round rod. Thus, in this case, the coupling element comprises two parts, of which one, i.e. the encompassing member, cooperates with the connecting headpiece, and the other part, i.e. the connecting member, is provided for the mechanical connection between the encompassing member and the holding device. The connecting member is suitably integrally formed with the encompassing member. The connecting member has a free end adapted for connection with the holding device against unintended detachment. For this purpose, the free end is provided with at least one and preferably a plurality of locking projections arranged for engagement behind the edge of an opening in the holding device. The connecting member can be inserted into the opening of the holding device to a larger or smaller extent so that the distance of the encompassing member from the holding device can be suitably selected corresponding to the respective conditions. Normally, for application devices having supply reservoirs which are different in their diameter and axial length, use has to made of different holding devices because the syringe bodies are usually supported on the holding devices by clamping attachment, i.e. the latter are adapted to the diameter of the syringe bodies; because of the variability of the length and due to the fact that application devices operated with different syringe bodies can be used with the same connecting pieces, the selfsame coupling element can be used in all of these application devices.

According to a preferred embodiment of the invention, it is provided that the holding device comprises grip-under projections projecting from the plane of the supply reservoirs held by the holding device, and that the holding device is provided with holding receiving portions arranged to have the supply reservoirs pressed and/or locked thereinto.

In the above embodiment of the invention, the grip-under projections extend out of the plane defined by the substantially cylindrical supply reservoirs and their longitudinal axes, respectively, or—other words—extend at right angles to this plane. Thereby, the distance existing between the index and middle fingers when these are in gripping engagement under the projections while holding the application device during discharge of adhesive, is considerably reduced in comparison to known devices and holding means, which noticeably facilitates the handling particularly for persons who have small hands.

In addition to the function of holding the supply reservoirs in position relative to each other, the holding device according to this embodiment of the invention fulfills the objective to allow the whole application device to be easily held by hand by having one's index and middle fingers gripping under the projections of the holding device. The (grip-under) projections suitably extend only in the region between adjacent supply reservoirs and resp. adjacent holding receiving portions of the holding device. Inserting the supply reservoirs is extremely simple since they merely have to be (laterally) pressed and/or locked into the holding receiving portions. It is not required to axially move and/or twist the supply reservoirs into a end position for holding so as to lock them to the holding device.

The holding device can be advantageously configured in the manner of a holding clip comprising elastically formed receiving portions for insertion or removal of the supply reservoirs. These receiving portions are suitably C-shaped, with each C-shaped receiving portion (also referred to as a clamp hereafter) extending through more than 180° and gripping the associated supply reservoir by clamping. These open holding receiving portions allow the supply reservoirs to be easily and simply pressed thereinto, to be held by clamping thereafter because of the elasticity of the receiving portions. The openings of the receiving portions can be directed to sides averted from each other or to a common side of the holding device, or they are oriented at a different other angle. The grip-under projections are located between the openings of the holding receiving portions without obstructing the access to the openings.

In the above described embodiment, the holding device is arranged for sliding displacement on the supply reservoirs. For limiting the movement of the holding device towards the rear end of the supply reservoirs which have a respective piston rod projecting therefrom, cooperating stoppers are provided on the holding device and the rear end of the supply reservoirs. On the supply reservoirs, these stoppers are the mutually averted flanges of the syringe bodies, which flanges are a customary part of the syringe bodies. These flanges will have the holding device abutting thereon so that a further relative movement towards the ends of the piston rods is excluded.

The connecting headpieces mostly used in application devices o the presently discussed type are normally provided, in addition to the channels for the components of the tissue adhesive, with a channel for a medical gas (oxygen). Also this gas channel comprises a gas connector and a gas outlet on the discharge end of the connecting headpiece.

Suitably, the discharge end of the connecting headpiece has a cannula or a catheter connected thereto. In case of a multi-lumen arrangement of this catheter or resp. cannula, care must be taken to have the lumina on the discharge end of the connecting head arranged flush with the component channels and resp. the gas channel.

By way of alternative to a cannula and resp. a catheter, the connecting headpiece can be connected also to a spraying head and resp. a spraying device by which the components can be mixed and sprayed. The atomization of the components can be performed in a purely mechanical manner (by a corresponding configuration of the discharge openings) or by use of a medical gas.

The embodiments of the invention described above in connection with the application device pertain as well to the holding device as such which likewise forms part of the invention.

BRIEF DESCRIPTION OF THE DRAWINGS

The present invention will now be explained hereunder in greater detail with reference to the drawings wherein.

DETAILED DESCRIPTION OF THE INVENTION

Figure 1:
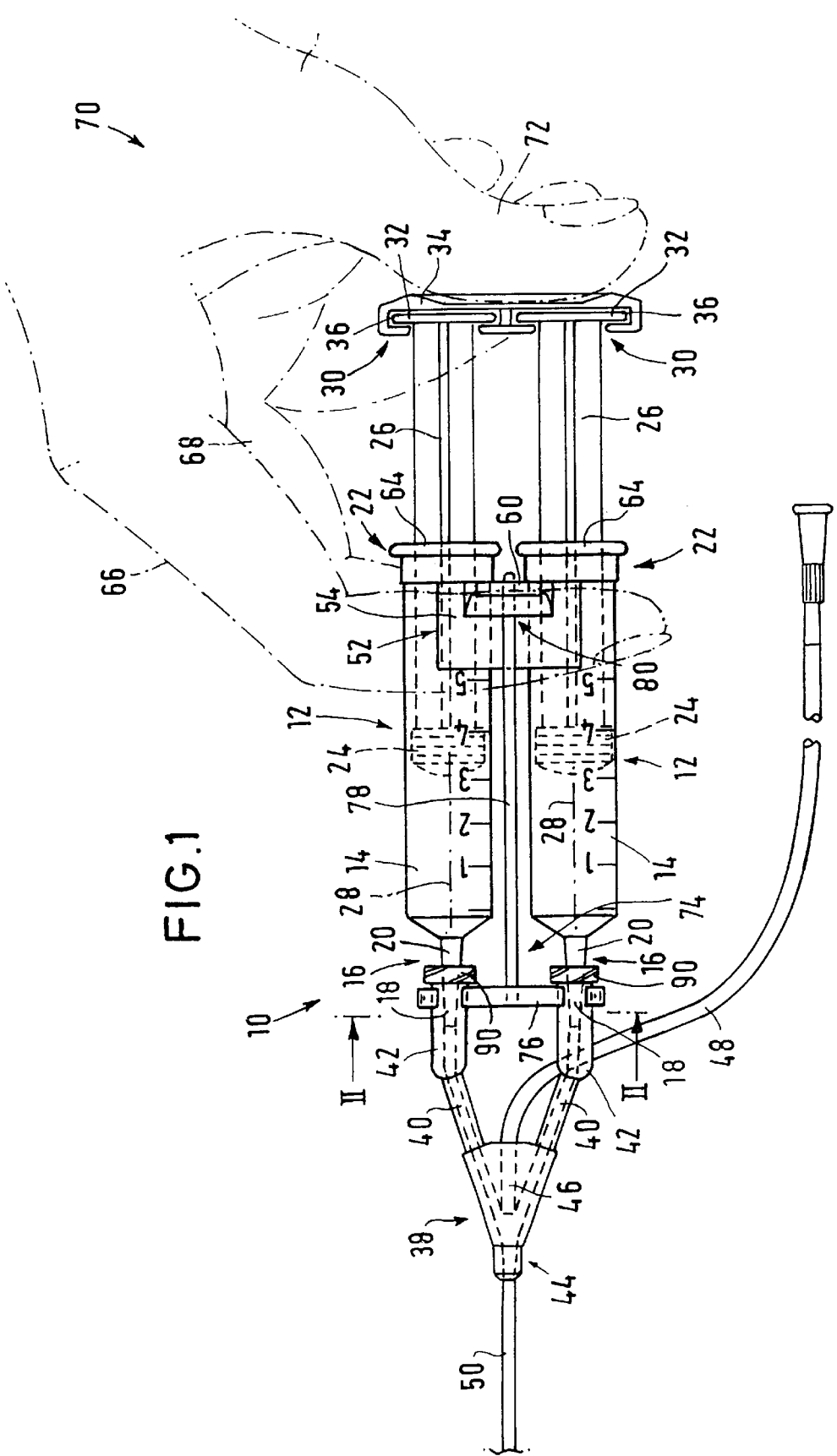
FIG. 1 is a side view of the application device with a hand shown in chain-dotted lines in its gripping position for holding and actuating the application device.

FIG. 1 is a side view of an application device 10 for multicomponent tissue adhesives. Application device 10 comprises two supply reservoirs in the form of usual commercially available syringes 12 for solutions of proteins and blood-coagulation-promoting coagulation factors of a two-component tissue adhesive. Each syringe is provided with a hollow cylindrical syringe body 14 comprising a front end 16 with and outlet opening 18 and a connecting piece 20, and an open rear end 22. Each syringe body 14 has arranged therein a piston 24 which is in sealing abutment on the inner surface of syringe body 14 and is held by a piston rod 26 guided out of syringe body 14 through the rear end 22. The piston rods 26 extend respectively in the longitudinal dimension of the syringe bodies 14 the longitudinal axes 28—outlined in the Figures—of the syringe bodies 14). The free ends 30 of the piston rods 26 facing way from the piston 24 are provided with annular flanges 32. The annular flanges 32 are mechanically connected to each other by a connecting element 34. Connecting element 34 is provided with two holding receiving portions 36 which are laterally open and suited for insertion of the annular flanges 32.

The slightly conical connecting pieces 20 on the front ends 16 of the syringe bodies 14 have a connecting headpiece 38 mounted thereon. Connecting headpiece 38 is provided with integrally formed channels 40 extending therethrough, indicated by chain-dotted lines. The channels 40, on their accommodating connecting pieces 42 facing towards the syringe bodies 14, are arranged at corresponding distances from the connecting headpieces 20 of the syringe bodies 14, and on their discharge end 44 facing away from the syringe bodies 14 are arranged immediately adjacent each other. Further, connecting headpiece 38 is formed with a further channel 46 connected to a hose 48 for the supply of a medical gas (e.g. $O_2$). Also this channel ends on the discharge end 44 in the immediate vicinity of the two other channels 40. The connecting headpiece 38 is provided with a three-lumen catheter 50 having its three lumina arranged flush with the three channels 40 and 46 of connecting headpiece 38.

As evident from the Figures, the two syringe bodies 14 are connected to each other by a clip holding device 52 (hereunder referred to as a holding element). The holding element 52 is provided with two C-shaped holding clamps 54 having their openings 56 facing away from each other and being connected to each other in their central portions (also FIG. 2). The openings 56 are oriented in the direction of the extension of the plane 28 in which the longitudinal axes of the syringe bodies 14 are arranged. Connected to the holding clamps 54 are grip-under projections 60. These projections 60 extend in mutually opposite directions and are turned at an angle of 90° relative to the two holding clamps 54 or the openings 56 of the clamps. Thus, the two projections 60 respectively project at right angles from the plane 58 in which the longitudinal axes 28 of the syringe bodies 14 are arranged while held by the holding element 52 and in which the longitudinal axes of the clamps 54 extend while coinciding with the longitudinal axes 28 of the syringe bodies 14. Therefore, the projections 60 extend in opposite directions along the axis of symmetry 62 of the dual clamp arrangement (also FIG. 2).

The syringe bodies 14 are supported on the holding element 52 for sliding displacement because the resilient elastic holding clamps 54 extend by more than 180° and preferably by up to 200° around the syringe body 14, thus encompassing the syringe body with a clamping force which allows for a displacement. Holding element 52 is arranged to abut with the laterally projecting flanges 64 on the rear ends 22 of the syringe bodies 14, thus providing for a stopper between holding element 52 and syringe body 14. The axial extension of the holding element 52 and particularly of the holding clamps 54 is dimensioned such that the measuring scale arranged externally on the syringe bodies 14 is left visible and unobstructed.

The whole device 10 inclusive of the connecting head 38 is made of plastic.

The position of the hand when manipulating the device 10 for holding and actuating it is outlined in FIG. 1. The device 10, i.e. the dual syringe arrangement of device 10, is held between the index and middle fingers 66, 68 of a hand 70 while the thumb 72 of hand 70 is in abutment on connecting element 34. The projections 60 of holding element 52 are engaged thereunder by the index and middle fingers 66, 68 of the hand 70, i.e. the fingers abut the side of projections 60 facing away from connecting element 34. When pressing on the connecting element 34 by means of the thumb 72, the pistons 24 are advanced in the direction towards the front ends 16 of the syringe bodies 14, with the holding element 52 being acted on by the flanges 64 in the manner of an abutment or stopper. As can be seen in FIG. 1, the index and middle fingers 66, 68 need only be spread by a width corresponding to the outer diameter of the syringe body 14 for handling the device 10. This is noticeably easier than having one's fingers 66, 68 spread by the amount of the largest transverse dimension of device 10 (i.e. by twice the outer diameter of the syringe bodies 14 plus the distance between the two syringe bodies 14). Thus, the device 10 as described herein and illustrated in the drawings is easily handled particularly by persons with small fingers.

Figure 2:
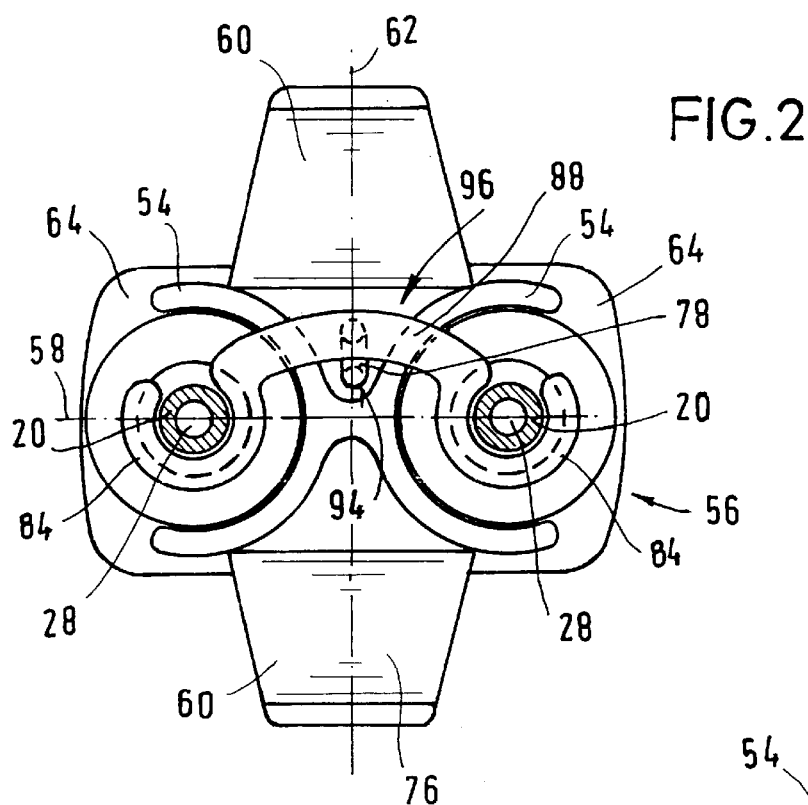
FIG. 2 is a sectional view of the application device taken along the line II—II of FIG. 1.

As evident from FIGS. 1 and 2, the holding element 52 and the connecting headpiece 38 are connected to each other by a coupling element 74. The coupling element 74 comprises an encompassing member 76 and a connecting member 78 which integrally connected thereto and has its free end 80 connected to the holding element 52 (also FIG. 3). The encompassing member 76 comprises two encompassing zones 82 formed respectively as resiliently elastic round brackets 84 extending at an angle of up to 270° and being open at 86. Both openings 86 are facing substantially in the same direction. The two round brackets 84 are integrally connected to each other by a crossbar 88.

The two openings 86 of the encompassing member 76 are adapted to mount the latter to the accommodating connecting pieces 42 of the connecting headpiece 38 from the side. In the process, the round brackets 84 are brought into engagement behind radial projections 90 formed on the accommodating connecting pieces 42 and provided as male portions of a luer lock device. When the connecting member 78 has been fixedly connected to the holding element 52 and the encompassing member 76 has been mounted to the accommodating connecting piece 42, the connecting headpiece 38 is thus secured against undesired detachment from the connecting piece 20 of syringe body 14.

Figure 3:
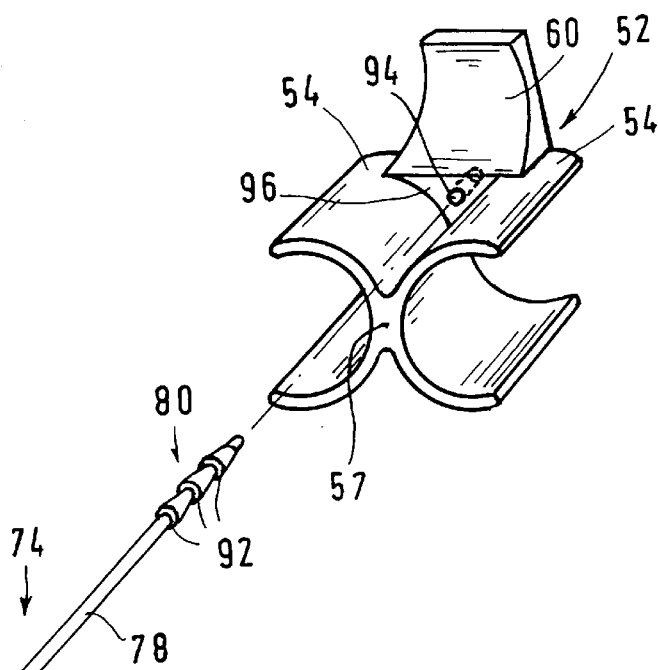
FIG. 3 is a perspective, exploded view of the coupling element and the holding device.
Figure 3:
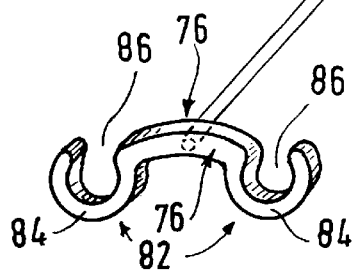

As shown in FIG. 3, the free end 80 of connecting member 78 is provided with a plurality of locking projections 92. The coupling of the connecting member 78 to the holding element 52 is performed by inserting the free (locking) end 80 of the connecting member 78 into a bore 94 of the holding element 52. This bore 94 is formed in one of the two gripping (grip-under) projections 60 of holding element 52, notably in the (inner) region 96 of projection 60, wherein this region 96 is limited by the two C-shaped holding clamps 54 and their back portion 57. The locking projections 92 are hooked in the bore 94 and are in engagement behind its edge near the side of holding element 52 facing away from encompassing member 76. The farther the free end 80 of connecting member 78 in shifted through the bore 94, the more the distance between the encompassing member 76 and the holding element 52 is reduced. Thus, the effective length of the coupling element 74 can be adapted to the distance between the radial projections 90 of the connecting headpiece 38 (which are to be engaged by the encompassing member 76 therebehind) and the flanges 64 of the syringe bodies 14 (whereon the holding element 52 should abut).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An application device for dispensing a multicomponent tissue adhesive, which comprises
   a plurality of supply reservoirs for respective fluid components, each supply reservoir having a front end provided with an opening for discharging the respective fluid components and a rear end disposed opposite to the front end,
   a piston arranged for sliding displacement in the supply reservoirs, said piston comprising a piston rod projecting from said rear end and having an actuating end for actuating the piston,
   a connecting headpiece having accommodating their front ends for communication with the front ends of the supply reservoirs, the connecting headpiece having separate channels for accommodating; the individual fluid components
   a discharge end disposed at the end of the connecting headpiece for the simultaneous discharge of all fluid components,
   a holding device for holding the supply reservoirs in the region of their rear ends and the connecting headpiece in the region of the connecting pieces,
   a coupling element for releasably connecting the holding device to the connecting headpiece at one end thereof, said coupling element including an encompassing member which defines a plurality of encompassing zones for at least partially encompassing and engaging the accommodating connecting pieces, and for abutting engagement with the holding device at the other end thereof.

2. The application device according to claim 1, wherein the coupling element comprises a connecting member which is connected at one end to the encompassing member and at the other end to the holding device.

3. The application device according to claim 2, wherein the connecting member is integrally connected at said one end to the encompassing member and said other end is provided with at least one locking projection for locking engagement with the holding device.

4. The application device according to claim 3, wherein the connecting member contains a plurality of locking projections arranged in series along the connecting member.

5. The application device according to claim 3, wherein the holding device contains a locking hole for receiving said other end of said connecting member.

6. The application device according to claim 1, wherein the accommodating connecting pieces of the connecting headpiece are provided with projections which are arranged as annular flanges.

7. The application device according to claim 6, wherein the annular flanges are arranged as male luer lock devices.

8. The application device according to claim 1 wherein the pistons are provided with piston rods which are connected to each other by a common connecting element and thus actuated together.

9. The application device according to claim 8, wherein the common connecting element comprises laterally open receiving spaces adapted to accommodate flanges arranged at the free ends of the piston rods.

10. The application device according to claim 1, wherein the plurality of encompassing zones are elastic to allow lateral mounting on the accommodating connecting pieces.

11. The application device according to claim 1, wherein each encompassing zone comprises a curved elastic bracket extending along an angular range between about 200° and about 300°.

12. The application device according to claim 1, wherein the curved elastic bracket is a continuous piece.

13. The application device according to claim 1 wherein the holding device comprises projections extending away from each other and adapted to be gripped by the fingers of a hand, said projections extending out of a plane in which the supply reservoirs held by the holding device are arranged.

14. The application device according to claim 1 wherein the holding device comprises holding receiving portions for pressing and locking the supply reservoirs therein.

15. The application device according to claim 1 wherein the holding device and the supply reservoirs are provided with stopper means for limiting a relative movement of the holding device and the supply reservoirs in the direction of the rear ends of the supply reservoirs.

16. The application device according to claim 1 wherein the supply reservoirs are held by the holding device for slidable displacement therein.

17. The application device according to claim 1 wherein the supply reservoirs have their rear ends provided with projecting flanges for contact with the holding device.

18. The application device according to claim 1 wherein the holding device comprises two mutually connected and symmetrically arranged C-shaped clamps which open away from each other for clamping engagement around two supply reservoirs traversing more than 180°, said two mutually connected C-shaped clamps containing two projections extending away from each other and along the axis of symmetry of the two C-shaped clamps.

19. The application device according to claim 1 wherein the coupling element and the holding device are made of an elastic material.

20. The application device according to claim 1 wherein the connecting headpiece includes a gas connector for the supply of a medical gas, and a channel communicating with the gas connector and extending from the gas connector to the discharge end of the connecting headpiece.

21. The application device according to clam 1 wherein the discharge end of the connecting headpiece has connected thereto a cannula.

22. A holding device used for facilitating the dispensing of a multicomponent fluid from a fluid applicator containing a plurality of liquid supply reservoirs operatively connected to a connecting headpiece, said holding device comprising
   mutually connected and symmetrically arranged clamps which define apertures which face away from each other, each of said clamps being adapted to accommodate a liquid supply reservoir, two projecting elements for accommodating the fingers of a user, each projecting element extending from said clamps in mutually opposite directions along an axis of symmetry of the clamps, an encompassing member defining encompassing zones which are adapted for engagement with the connecting headpiece, and a coupling element extending from the encompassing member to the clamps to provide a means for securing the encompassing member to said clamps, thereby providing stability between the liquid supply reservoirs and the connecting headpiece.

23. The holding device according to claim 22, wherein the coupling element is provided with at least one locking projection for locking connection to the clamp.

24. The holding device according to claim 23, wherein the clamps are provided with a locking hole adapted to receive the locking projection.

25. The holding device according to claim 24, wherein the connecting element contains a plurality of locking projections arranged in series along the connecting element.

26. The holding device according to claim 22, wherein the encompassing member is elastic to allow lateral mounting on the connecting headpiece.

27. The holding device according to claim 22, wherein the encompassing member comprises an elastic bracket extending along an angular range between about 200° and 300°.

28. The holding device according to claim 22, wherein the encompassing member is a curved bracket.

29. The holding device according to claim 22, wherein the clamps are adapted to press and lock the supply reservoirs therein.

30. The holding device of claim 22, wherein the elastic material is a plastic material.

* * * * *